United States Patent
Kurtz

(10) Patent No.: US 6,261,597 B1
(45) Date of Patent: Jul. 17, 2001

(54) METHOD FOR TREATING PERIODONTAL DISEASE

(76) Inventor: Seymour J. Kurtz, 211 E. Ontario St., Suite 1195, Chicago, IL (US) 60611

(*) Notice: Subject to any disclaimer, the term of this patent is extended or adjusted under 35 U.S.C. 154(b) by 0 days.

(21) Appl. No.: 09/453,494

(22) Filed: Dec. 3, 1999

Related U.S. Application Data

(63) Continuation of application No. 08/703,333, filed on Aug. 30, 1996, now abandoned.
(60) Provisional application No. 60/003,046, filed on Aug. 31, 1995.

(51) Int. Cl.$^7$ ..................................................... A61K 9/127
(52) U.S. Cl. .......................... 424/450; 424/581; 514/78; 514/900; 604/51; 604/52
(58) Field of Search .................... 424/450, 581; 514/78, 900; 604/51, 52

(56) References Cited

U.S. PATENT DOCUMENTS

| | | | |
|---|---|---|---|
| 4,812,314 | * 3/1989 | Barenholz et al. | 424/450 |
| 5,324,520 | * 6/1994 | Dunn et al. | 424/435 |
| 5,489,611 | * 2/1996 | Lee et al. | 514/557 |
| 5,622,715 | * 4/1997 | Barenholz et al. | 424/450 |
| 5,965,157 | * 10/1999 | Li et al. | 424/450 |

OTHER PUBLICATIONS

Williams, K.J., Werth, P. and Wolff, J.A. Intravenously administered lecithin liposomes: a synthetic antiatherogenic lipid particle. 1984. Perspectives in Biology and Medicine, 27, 3, pp. 417–431.*

\* cited by examiner

*Primary Examiner*—Thurman K. Page
*Assistant Examiner*—Liliana Di Nola-Baron
(74) *Attorney, Agent, or Firm*—Foley & Lardner

(57) ABSTRACT

A method of improving the periodontal condition of a person is disclosed. A suspension of small, unilamellar vesicles composed primarily of phospholipids, similar in nature to those of egg phosphatidylcholine, is administered parenterally to a person suffering from periodontal disease. In the method, liposomes are infused over an extended period of time of at least several weeks, until a desired improvement in gum condition is achieved.

5 Claims, 1 Drawing Sheet

METHOD FOR TREATING PERIODONTAL DISEASE

This application is a continuation of application Ser. No. 08/703,333, filed Aug. 30, 1996, now abandoned.

This application claims the benefit of U.S. Provisional Application No. 60/003,046, filed Aug. 31, 1995.

FIELD OF THE INVENTION

The present invention relates to methods for improving the periodontal health of a subject by intravenous administration of a suspension of liposomes. The invention also relates to methods for improving hair regrowth of a subject by intravenous administration of a suspension of liposomes.

REFERENCES

Amselem, S., et al., *LIPOSOME TECHNOLOGY* (Gregoriadis, G., Ed.), pp. 501–524, CRC Press, Boca Raton, Fla. (1993).

Barenholz, Y., et al., *Biochemistry* 16:2806 (1977).

Barenholz, Y., et al., *LIPOSOME TECHNOLOGY* (Gregoriadis, G., Ed), pp. 524–607, CRC Press, Boca Raton, Fla. (1993).

Daida, H., et al., *Am. J. Cardiol.* 73(15):1037–1040 (1994).

Desmarais, R. L., et al., *Circulation* 91(5):1403–1409 (1995).

Groop, P. H., et al., *Diabet. Med.* 11(10):961–967 (1994).

Harrison, T. R., Ed., *HARRISON'S PRINCIPLES OF INTERNAL MEDICINE, TWELFTH EDITION*, pp. 1001–1015, McGraw Hill, Inc. (1991).

Kokoglu, E., et al., *Cancer Biochem. Biophys.*, 14(2):133–136 (1994).

Levida, M., *HANDBOOK OF NUTRITION IN THE AGED* (Watson, R. R., Ed.), CRC Press, pp. 89–109 (1985).

Shinitsky, M., et al., *J. Biol. Chem.* 249:2652 (1974).

Szoka, F., et al., *Ann. Rev. Biophys. Bioeng.* 9:467 (1980).

Takahashi, S., et al., *Ann. Rheum. Dis.* 54(2):90–93 (1995).

Tenda, K., et al., *Jpn. Circ. J.* 57(8):789–795 (1993).

Yamamoto, K., et al., *Metabolism* 44(1):4–7 (1995)

BACKGROUND OF THE INVENTION

There are several classes of globular, lipid-containing particles, known as lipoproteins, that circulate in human blood and transport nonpolar lipids, primarily triglycerides and cholesteryl esters, through the plasma. Lipoproteins are classed according to the composition of the nonpolar lipids in the core of the particle and according to the composition of the apoproteins on the surface, and the density size and electrophoretic mobility of the lipoprotein (Harrison, 1991).

Recent studies have shown various disease associations with above-normal or sub-normal levels of certain lipoproteins. It is known, for example, that serum Lp(a) is elevated in subjects with gout (Takahashi, et al., 1995), various types of cancer, such as breast cancer (Kokoglu, et al., 1994), hyperthyroidism (Yamamoto, et al., 1995), and in Type 1 diabetics with early and established renal disease (Groop, et al., 1994). It has also been shown that there is a direct correlation between development of post-angioplasty restenosis and elevated serum Lp(a) concentrations (Tenda, et al., 1993).

SUMMARY OF THE INVENTION

In one aspect, the invention includes a method of reducing the Lp(a) concentration in a subject at risk for developing a disease condition associated with a chronic, elevated Lp(a) concentration, such as gout, breast cancer, hyperthyroidism, coronary heart disease or cerebral vascular disease. The method includes intravenously administering to the subject a suspension of small unilamellar liposomes composed primarily of phosphatidylcholine phospholipids having phase transition temperatures in the range between about −10 and 37° C., preferably a transition temperature of less than about 50° C., as exemplified by egg phosphatidylcholine (egg PC) which has a transition temperature of −5° C.

The liposomes in the composition are small unilamellar vesicles (SUV's), i.e., vesicles having sizes predominantly between 0.02 and 0.12 microns, and preferably 0.02–0.08 microns. The liposome suspension is administered at a dose of between about 50–1,000 mg lipid/kg body weight. Multiple treatments may be given, e.g., at least once a week, over a several week period. Treatment is carried out until a desired reduction in Lp(a) level is observed.

The treatment method may also be applied to a person having an elevated Lp(a) serum concentration and a disease, such as gout, breast cancer or hyperthyroidism, cerebral vascular disease, and coronary heart disease associated with such elevated concentrations.

In another aspect, the invention provides a method of inhibiting restenosis in a subject, following percutaneous transluminal coronary angioplasty or surgical resection of vascular tissue. The method includes administering liposomes, as described above, until a reduction in serum Lp(a) concentration is observed.

In another aspect, the invention includes a method of achieving hair regrowth in a person suffering from male pattern baldness or alopecia, and a method of improving the periodontal condition in a person having symptoms of periodontal disease, such as gingivitis, tooth mobility or bone loss.

In both methods, a suspension of liposomes of the type described above is administered until a significant improvement in the condition is observed.

These and other objects and features of the invention will be more fully appreciated when the following detailed description of the invention is read in conjunction with the accompanying drawings.

DETAILED DESCRIPTION OF THE INVENTION

I. Definitions

Figure 1A:
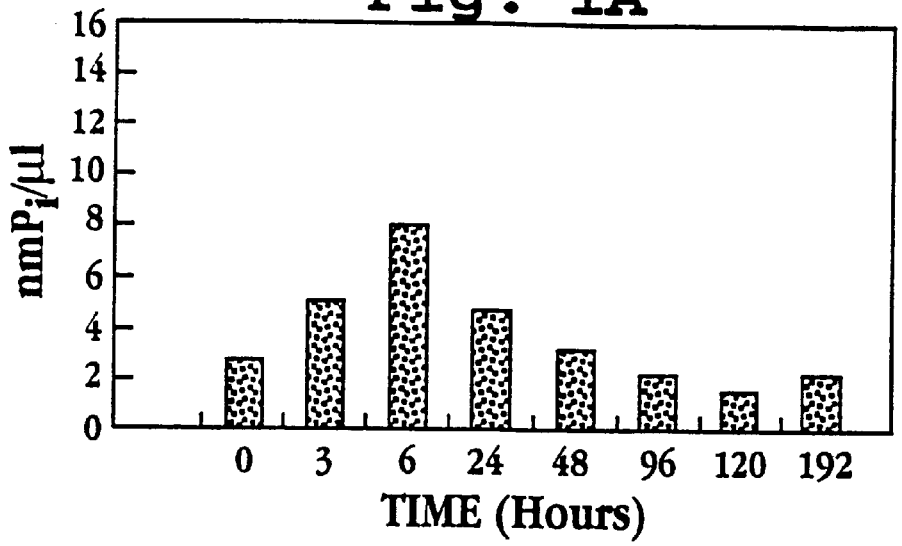
FIGS. 1A–1C are bar graphs showing serum phospholipid phosphorus levels in three human subjects (FIG. 1A, FIG. 1B, FIG. 1C, respectively) for a period of 8 days, where continuous liposome infusion occurs in hours 0–6.

The term "elevated Lp(a) concentration", as used herein, refers to a serum Lp(a) concentration above 25 mg/dl.

The term "chronic elevated Lp(a) concentration", as used herein, refers to a concentration of Lp(a) that is on average elevated above normal average serum Lp(a) concentrations when measured at various times over the course of a week. A normal average serum Lp(a) concentration is generally below 25 mg/dl.

The term "significant reduction in Lp(a) concentration", as used herein, refers to a reduction of at least 20k, preferably more than 40%, with respect to the pretreatment Lp(a) concentration in a subject.

II. Preparation of Liposomes

The invention includes, in one aspect, administering to a human subject a suspension of liposomes to reduce serum Lp(a) concentrations. The subject in need of such treatment is one having or at risk of developing a disease condition, such as those mentioned above, associated with a chronic, elevated Lp(a) concentration.

In one preferred embodiment, described and used in the examples below, the liposomes are composed predominantly (more than 50 mole percent, preferably more than 80–90 mole percent) of phosphatidylcholine (PC) having a phase transition temperature less than about 37° C., preferably between about −10 to 24° C., e.g., 5° C. or lower.

One preferred vesicle composition includes egg PC, which contains predominantly 1-palmitoyl, 2-oleyl PC and 1-palmitoyl,2-linoleyl PC. The liposomes may be composed entirely of the egg PC, which has a transition temperature of −5° C., or may contain other lipid components which (i) are not immunogenic, and (ii) do not contribute a significant portion, i.e., more than 25–50 mole percent, of lipids with high phase transition temperature. In the case where liposomes are composed of PC and one or more other lipid components, the phospholipids making up the liposome will have a collective phase transition temperature. In a preferred embodiment, the liposomes are composed of phospholipid, that is PC and one or more other lipid components, having a collective phase transition temperature of less than 5° C.

Additional components in the liposome composition may include negatively charged lipids, such as phosphatidylglycerol (PG) or phosphatidylserine (PS). Of course, the mole percentage of these lipids should be relatively low with respect to PC. The liposomes may also include cholesterol or other sterols, in an amount preferably less than about 40 mole percent.

Lipid protective agents, such as α-tocopherol, α-tocopherol acetate, or α-tocopherol succinate, may also be included in the lipids forming the liposomes, to protect the lipid components against free radical damage (Levida, 1985). Typically such agents are included at a mole percentage between about 0.05% and 2%. It is advantageous to add α-tocopherol to the liposomes to maintain a balance between vitamin E and polyunsaturated lipids in the liposomes.

A. Unsized Liposomes

A variety of methods for producing liposomes are available, and these have been extensively reviewed (Szoka, et al., 1980). In general these methods produce liposomes with heterogeneous sizes from about 0.02 to 10 microns or greater. As will be discussed below, liposomes which are relatively small and well defined in size are preferred for use in the present invention, hence a second processing step for reducing the size and size heterogeneity of liposomal suspensions will usually be required.

In one preferred method for forming the initial liposome suspension, the vesicle-forming lipids are taken up in a suitable organic solvent system, and dried in vacuo or under an inert gas to form a lipid film in a vessel. An aqueous suspension medium, such as a sterile saline solution, is added to the film, and the vessel is agitated until the lipids have hydrated to completion, typically within 1–2 hours. The amount of aqueous medium added is such as to produce a final liposome suspension containing preferably between about 10 and 30 g lipid per 100 ml media.

The lipids hydrate to form multilamellar vesicles (MLVs) whose sizes range between about 0.5 microns to about 10 microns or larger. In general, the size distribution of MLVs can be shifted toward slightly smaller sizes by hydrating the lipids under more vigorous shaking conditions. Example 1 describes the preparation of egg PC MLVs, prior to treating the MLVs with ultrasonic irradiation to reduce the liposome sizes.

The aqueous medium used in forming the liposomes may contain water-soluble agent(s) which enhance the stability of the liposomes upon storage. A preferred stabilizing agent is an iron-specific trihydroxamine chelating agent, such as desferrioxamine. The use of this compound in reducing lipid peroxidation and free radical damage in drug-containing liposomes has been reported in U.S. Pat. No. 4,797,285. Briefly, it was shown that the combination of a lipophilic free-radical quencher, such as α-tocopherol, and the water-soluble chelator gave better protection against lipid peroxidation damage than did either protective agent alone. The chelator is included in the aqueous medium in molar excess of the amount of free iron in the medium. Typically, a chelator concentration of between about 10–200 micromolar is sufficient.

B. Sizing Liposomes

The suspension of liposomes prepared as above is preferably treated to produce a desired liposome size and size homogeneity.

The liposome suspension may be sized to achieve a distribution of vesicles in a range less than about 0.12 microns and preferably less than about 0.08 microns.

Several techniques are available for reducing the sizes and size heterogeneity of liposomes, in a manner suitable for the present invention. Ultrasonic irradiation of a liposome suspension either by bath or probe sonication produces a progressive size reduction down to SUVs. A sonicating procedure used to produce SUVs is described in Example 1. Homogenization is another method which relies on shearing energy to fragment large liposomes into smaller ones. In a typical homogenization procedure, MLVs are recirculated through a standard emulsion homogenizer until selected liposome sizes, typically less than 0.1 microns, are observed.

Extrusion of liposomes through a small-pore polycarbonate membrane is an effective method of reducing liposome size down to a relatively well-defined size distribution. Sizes in a selected size range down to 0.03 microns can be achieved (Example 2) by extrusion through a polycarbonate membrane having a selected pore size, e.g., in the pore size range 0.03–0.1 microns. Typically, the suspension is cycled through the membrane several times until the desired liposome size distribution is achieved. The liposomes may be extruded through successively smaller-pore membranes, to achieve a gradual reduction in liposome size.

The size-processed liposome suspension may be readily sterilized by passage through a sterilizing membrane having a particle discrimination size of about 0.2 microns, such as a conventional 0.22 micron depth membrane filter. If desired, the liposome suspension can be lyophilized in the presence of a cryoprotectant for storage and reconstituted shortly before use. The final lipid concentration in the treatment composition is preferably about 10% (w/w). A suspension of greater than about 15% lipid (w/w) may be too viscous for practical iv infusion, and a suspension concentration significantly less than 10% will require a proportionately longer infusion time.

III. Treatment Method and Results

This section describes various treatment methods which involve intravenous administration of liposomes of the type described above. In these methods, liposomes are preferably infused two or more times during a period of at least two weeks, and at a dosing frequency of at least one time per week. A preferred dosing frequency is one–two times per week, although single-dose treatment is also contemplated. The dosing periods, e.g., two weeks, may be interrupted by a wash-out period, typically of 1–4 weeks. The treatment, e.g., involving repeating dosing and wash-out periods, may continue over an extended period of several months or more.

The amount of liposomes administered at each dose is between about 10–1,000 mg lipid per kg of body weight, and preferably between about 50–1,000 mg lipid per kg of body weight, although the dose may be substantially less. Long term dosages are typically delivered at a rate of between about 0.001–1 g lipid per kg body weight per day. In a preferred embodiment, the liposome suspension is administered one time per week, at a dose of about 200–500 mg lipid/kg body weight.

A typical dose for an 80 kg individual would be between about 10 and 80 grams lipid, corresponding to between 100 and 800 ml of 10% liposome (w/w) suspension. Administration may be by iv (intravenous) injection, but is preferably done by iv drip (infusion) over a period of at least about 1–2 hour, to minimize discomfort at the site of administration. The liposomes may be suspended in sterile saline or in a nutritional or drug-containing buffer or medium, such as a glucose/salt medium, to combine liposome treatment with other parenteral therapy.

Figure 1B:
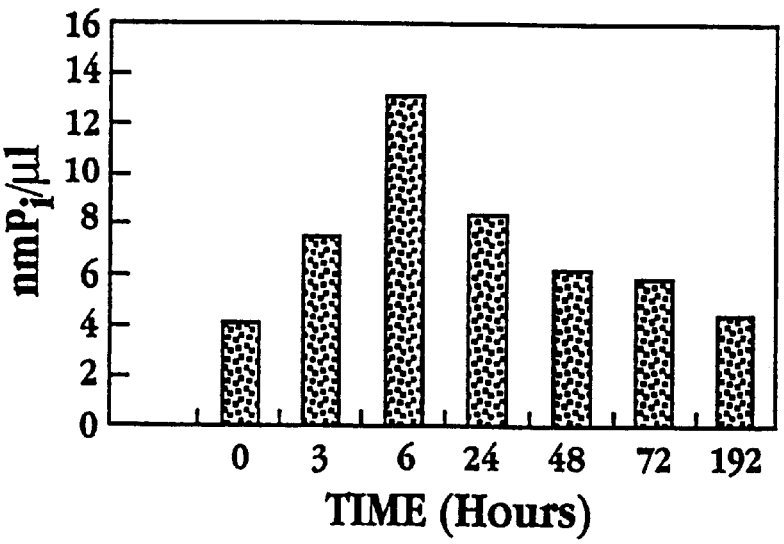
Figure 1C:
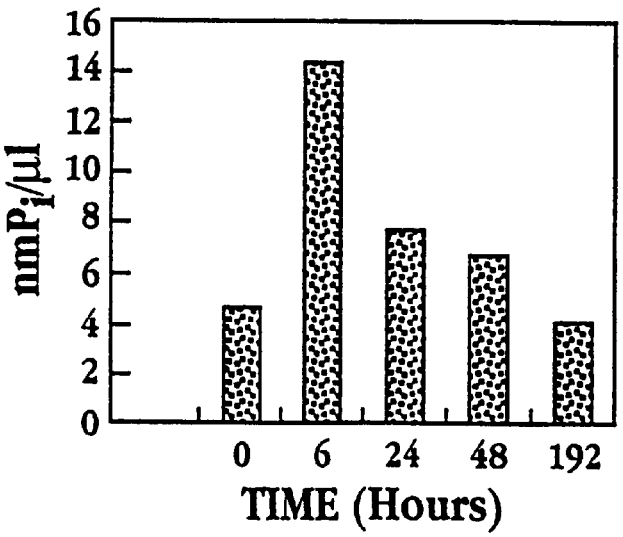

The method relies on the presence of administered liposomes in the bloodstream over an extended period following iv administration. Liposome levels in the blood following iv administration can be monitored by measuring serum levels of phospholipids, e.g., phosphorus. FIGS. 1A–1C show phospholipid phosphorus levels measured in three human subjects following a 6 hour iv infusion of liposomes. Liposomes, prepared as described in Example 1, were administered to each subject (FIG. 1A, 1B, and 1C, respectively) and serum phospholipid phosphorus and free cholesterol levels were monitored. Phospholipid phosphorus levels were measured prior to liposome infusion (time=0) to establish a base level in each patient. The liposomes were infused continuously over a period of 6 hours and blood samples were taken midway through the infusion period (time=3 hours) and at the end of infusion (time=6 hours). Post-infusion, each subject was monitored for 192 hours (8 days) and blood samples were taken at various times.

As seen, the concentration of liposomes in the bloodstream is greatest at the end of the infusion period (time=6 hours), and phosphorus levels greater than normal levels were observed for at least 48 hours post infusion, indicating the presence of exogenous circulating phospholipids. The results indicate that with a liposome infusion time of 6 hours, liposome dosing every two days would be effective in maintaining elevated liposome levels during the dosing period. However, it is noted that the dosing schedule can be more infrequent, since it is not necessary to maintain elevated liposome levels continuously in the treatment method.

A. Reducing the Risk of Diseases Associated with Lp(a)

In one aspect the invention provides a method of reducing the serum Lp(a) concentration in a person at risk for developing a disease condition associated with a chronic elevated serum Lp(a) concentration. Conditions associated with elevated Lp(a) concentrations include, for example, gout, breast cancer and hyperthyroidism. Coronary heart disease and cerebral vascular disease are other conditions associated with high Lp(a) levels.

A chronically elevated Lp(a) concentration refers to a serum Lp(a) concentration that is above about 25 mg/dl, typically representing an average of Lp(a) values, when measured several times over the course of a week. Serum Lp(a) concentrations can be measured by a variety of methods, including enzyme-linked immunoabsorbent assay (ELISA), latex immunoassay or immunoradiometric assay. A specific kit for determining Lp(a) concentration in a blood sample, Macra™, is available from Terumo Diagnostics (Elkin, Md.).

The treatment method, as applied to three male subjects, is described in Example 3. Briefly, each subject received a series of intravenous infusions of liposomes prepared as described in Example 1, and at the dose schedule described in Example 3. At times just before liposome infusion (0 hours) and 24 hours after liposome infusion (24 hours), Lp(a) concentrations were measured, with the results shown in Table 1. Although several time points were not measured, it is clear from the data that a significant reduction in Lp(a) was observed in all cases. For example, patient two, who had a relatively normal serum Lp(a) showed a drop from an initial concentration of 18 mg/dl to a concentration of 14 mg/dl at the end of the treatment period, i.e., a 29% drop in serum Lp(a) concentration. Subject 3 had an initial serum Lp(a) concentration of 32 mg/dl, a concentration in the elevated Lp(a) range. At the end of the treatment period, the Lp(a) concentration was reduced to 18 mg/dl, a 77% reduction.

TABLE 1

| Injection No. | Dose (mg/kg) | Time (hours) | Lp(a) (mg/dl) Subject 1 | Lp(a) (mg/dl) Subject 2 | Lp(a) (mg/dl) Subject 3 |
| --- | --- | --- | --- | --- | --- |
| 1 | 200 | 0 | — | 18 | 32 |
|   |     | 24 | — | — | 27 |
| 2 | 300 | 0 | — | — | 20 |
|   |     | 24 | — | — | 18 |
| 3 | 300 | 0 | — | 3.8 | — |
|   |     | 24 | — | 2.6 | 15 |
| 4 | 300 | 0 | — | 3 | 11 |
|   |     | 24 | — | 3 | 9 |
| 5 | 300 | 0 | 37 | 16 | 24 |
|   |     | 24 | — | 15 | — |
| 6 | 300 | 0 | — | 14 | 17 |
|   |     | 24 | — | — | 10 |
| 7 | 300 | 0 | 25.6 | — | — |
|   |     | 24 | 18.8 | — | 18 |

These results demonstrate the ability of the method to produce a significant reduction in serum Lp(a) levels.

B. Treatment of Diseases Associated with Elevated Lp(a)

In another aspect, the invention includes a method of treating gout, breast cancer, or hyperthyroidism in a subject having one of these conditions and an elevated serum Lp(a) concentration. Studies have shown that serum Lp(a) concentrations are elevated in many subjects with gout (Takahashi, et al., 1995), various types of cancer, such as breast cancer (Kokoglu, et al., 1994), and hyperthyroidism (Yamamoto, et al., 1995). The purpose of this method is to treat the clinical disease by lowering Lp(a) levels, as one of the underlying factors contributing to the disease.

Treatment, in accordance with the method of the invention, involves first determining serum Lp(a) concentration in a person having one of the above clinical conditions. A patient having an elevated Lp(a) level is then selected as a candidate for the liposome infusion method, as described above, typically as an adjuvant to another treatment method, such as surgery, chemotherapy, or radiation therapy in the case of breast cancer. Treatment is maintained until a significant reduction in Lp(a) is observed and preferably throughout the treatment period for the clinical disease.

C. Treatment of Restenosis

Restenosis occurs in approximately 20–30 percent of patients following percutaneous transluminal coronary angioplasty. Restenosis can also occur in patients following surgical resectioning of vascular tissue. In this procedure, a region of stenosis in a vessel is removed and the vessel is sutured closed. Restenosis in each case is apparently the result of excessive local myointimal hyperplasia, brought about by platelet aggregation to the freshly dilated or sutured vessel surface (Harrison, 1991).

Recent studies have shown that high serum Lp(a) concentrations are associated with an increased incidence of restenosis after balloon angioplasty (Daida, et al., 1994; Desmarais, et al., 1995; Tenda, et al., 1993). In one study, patients with a serum Lp(a) level of 38 mg/dl had a significantly higher level of restenosis than patients with a serum level of 19.9 mg/dl (Tenda, et al., 1993).

The present invention includes a method a reducing the extent of restenosis following procedures such as balloon angioplasty or surgical resectioning of vascular tissue. Typically in the method, a person undergoing such a procedure that can lead to restenosis is given one or more pretreatment infusions of liposomes, particularly where existing Lp(a) levels are elevated, to achieve a reduction in such levels. Following the procedure, the patient is again monitored for Lp(a) serum concentrations, and given further liposome infusions if necessary to maintain or achieve low Lp(a) levels, e.g., 20 mg/dl or lower. The treatment may be discontinued after a period of several weeks or more when the risk of restenosis has passed.

D. Treatment of Periodontal Disease

The invention also includes a method of improving the periodontal condition of a person suffering from periodontal disease, as evidenced, for example, by gingivitis, bone resorption, pocket formation or tooth mobility.

Liposomes were administered, in accordance with the method of the invention, to a male subject having a history of periodontal disease, as evidenced by severe bleeding gingiva, Class II and III mobility and pocket depths between 4–8 mm. Liposomes were infused according to the dosing schedule described in Example 3, and following treatment a significant improvement in the patient's dental health was observed. Periodontal pocket depths decreased to between 2–4 mm, except around two teeth where the pocket depth remained at 8 mm. Periodontal scaling and root planing indicated that very little bleeding was present, and teeth mobility was reduced to Class I.

Treatment by liposome administration may be continued until a desired improvement in gum condition is achieved.

E. Hair Regrowth

In another aspect, the invention includes a method of improving hair regrowth in a person having alopecia or male pattern baldness.

An elderly male subject with scalp hair loss was treated with liposomes, administered according to the dosing schedule described in Example 3. The subject noticed a significant improvement in hair regrowth after liposome treatment.

The following examples illustrate various methods for preparing liposome compositions and using the compositions in the treatment method of the invention. The examples are intended to illustrate, but in no way limit, the scope of the invention.

Materials

Egg phosphatidylcholine (egg PC) recovered from egg yolk was prepared according to known methods (Shinitsky, et al., 1974). High purity egg PC may also be purchased from Avanti Polar Lipids (Alabaster, Ala.) or Lipoid KG (Ludwigshafen, Germany). The egg PC was determined to be greater than 99% pure, based on thin layer chromatography (TLC) analysis. The egg PC fatty acid composition was similar to the reported composition. The main PC,s of the preparation included 1-palmitoyl,2-oleyl PC and 1-palmitoyl,2-linoleyl PC. Thin-layer chromatography plates, 0.25 silica gel HR and 0.024 silica gel, were obtained from Merck (Darmstadt, Germany) and Analtech (Newark, Del.) respectively.

EXAMPLE 1

Preparation of Small Unilamellar Vesicles: Sonication

Egg PC dissolved in chloroform was placed in a 100 ml vessel and dried to a thin film under nitrogen. Sterile saline was added to the lipid film to a final concentration of about 100 mg/ml, and the lipid film was hydrated with swirling. The resulting multilamellar vesicle (MLV) suspension was then bath sonicated for 1 hour using a Heat System Sonicator, Model 375W, at a power setting of 40–50% full value. The temperature of the suspension was maintained at about 4° C. under nitrogen during sonication. The sonicated suspension was separated from large vesicles by ultracentrifugation at 100,000 g for 1 hour (Barenholz, et al., 1977). The suspension of SUVs, having a concentration of about 100 mg/ml, was filter sterilized.

EXAMPLE 2

Preparation of Small Unilamellar Vesicles: Extrusion

Homogeneous small unilamellar vesicles of egg PC with an average diameter of 39±8 nm, in 0.15 M NaCl were prepared by extrusion using serial filtration through polycarbonate filters in a GH 76–400 pressure cell (Nucleopore, Pleasanton, Calif.) (Amselem, et al., 1993). Liposomal size was determined using a Coulter model N4 sub-micron particle analyzer equipped with a size distribution processor analyzer (Barenholz, et al., 1993). The final extrusion step was through a 0.05 micrometer pore polycarbonate filter. Egg PC SUV's were sterilized by filtration through sterile 0.22 micrometer Millipore filters.

EXAMPLE 3

Effect of Egg PC SUV Treatment on Lp(A)Serum Concentrations

Liposomes prepared as described in Example 1 were administered to three male subjects, identified herein as subjects 1, 2 and 3, having ages 40, 54 and 64 years, respectively.

At the start of treatment, each subject was given a 250 ml intravenous infusion of 0.9% saline followed by intravenous infusion of SUV liposomes at a dose of 200 mg lipids/kg body weight. Once a week for the next three weeks, each subject received by intravenous infusion 300 mg/kg of liposomes. After a 3–4 week washout period, each subject received 300 mg/kg of liposomes one time per week for three weeks. Table 1 summarizes the treatment regimen and shows the serum Lp(a) concentration of each subject during the course of treatment.

While various embodiments of the invention have been described herein, it will be apparent that various modifications can be made without departing from the intended scope of the invention.

What is claimed is:

1. A method of improving the periodontal condition of a person suffering from periodontal disease, comprising intravenously administering to the subject a suspension of small unilamellar liposomes composed predominantly of phosphatidylcholine phospholipids having phase transition temperatures in the range between about −10° C. and 37° C., and repeating said administering over a period of at least two weeks, and in an amount effective to achieve a desired improvement in gum condition.

2. The method of claim 1, wherein said administering includes administering liposomes having sizes ranging between 0.02 and 0.12 microns.

3. The method of claim 1, wherein said administering includes administering liposomes composed of egg phosphatidylcholine.

4. The method of claim 1, wherein said administering includes administering liposomes composed of phospholipid having a phase transition temperature less than about 5° C.

5. The method of claim 1, wherein said repeating includes administration of said liposome suspension at least one time per week and at a dose of between about 50–1,000 mg lipid/kg body weight.

* * * * *